United States Patent [19]

Loney et al.

[11] Patent Number: 5,137,517
[45] Date of Patent: Aug. 11, 1992

[54] DEVICE AND METHOD FOR GRIPPING MEDICAL SHAFT

[75] Inventors: Carol Loney, St. Louis Park; Richard C. Mattison, Rockford; David B. Robinson, Chanhassen, all of Minn.

[73] Assignee: SciMed Life Systems, Inc., Maple Grove, Minn.

[21] Appl. No.: 704,668

[22] Filed: May 20, 1991

Related U.S. Application Data

[63] Continuation of Ser. No. 442,246, Nov. 28, 1989, abandoned.

[51] Int. Cl.⁵ .................................................. A61M 5/178
[52] U.S. Cl. .................................... 604/159; 606/1; 24/115 M; 24/136 R
[58] Field of Search ............... 604/95, 159, 165, 170, 604/249, 250, 283; 128/656-658, 772; 606/1, 108, 144, 147; 24/115 R, 115 F, 115 G, 115 M, 136 R; 226/127, 158, 162; 254/134.3 R, 134.3 F T

[56] References Cited

U.S. PATENT DOCUMENTS

| | | | |
|---|---|---|---|
| 904,863 | 11/1908 | Glass et al. | 24/136 R |
| 1,238,167 | 8/1917 | McIntyre | 24/136 R |
| 2,220,203 | 11/1940 | Brarin | 24/136 R |
| 3,070,057 | 12/1962 | Dezzani | 226/156 |
| 3,312,128 | 4/1967 | Wasson . | |
| 3,452,740 | 7/1969 | Muller . | |
| 3,682,173 | 8/1972 | Center | 604/159 |
| 3,915,167 | 10/1975 | Waterman | 604/250 |
| 3,960,149 | 6/1976 | Bujan | 604/250 |
| 4,057,186 | 11/1977 | Hedger | 226/127 |
| 4,598,708 | 7/1986 | Beranek . | |
| 4,664,115 | 5/1987 | Ohachi | 606/1 |
| 4,726,369 | 2/1988 | Mar . | |
| 4,799,496 | 1/1989 | Hargreaves et al. . | |
| 4,829,999 | 5/1989 | Auth . | |
| 4,858,810 | 8/1989 | Intlekofer et al. | 604/159 |
| 4,874,371 | 10/1989 | Comben et al. . | |
| 4,957,117 | 9/1990 | Wysham | 604/95 |

OTHER PUBLICATIONS

Flyer: "Hartzler Micro II Dilation Catheters" of Advanced Cardiovascular Systems, Inc., 1988.

*Primary Examiner*—John D. Yasko
*Assistant Examiner*—Anthony Gutowski
*Attorney, Agent, or Firm*—Kinney & Lange

[57] ABSTRACT

A device for gripping a medical shaft such as a guide wire or catheter tube has two operative components: a body member with a longitudinal slot for receiving the shaft and an insert member slidably received in the slot of the body member. The body member and insert member have opposed, generally parallel shaft engagement surfaces which extend longitudinally along the shaft on each side thereof. Moving the insert member longitudinally relative to the body member activates a slide arrangement which moves the opposed surfaces laterally toward one another to grip the shaft therebetween while remaining generally parallel.

25 Claims, 4 Drawing Sheets

DEVICE AND METHOD FOR GRIPPING MEDICAL SHAFT

This is a continuation of application Ser. No. 07/442,246, filed on Nov. 28, 1989, abandoned as of the date of this application.

BACKGROUND OF THE INVENTION

This invention relates to the field of medical devices and, in particular, devices for gripping small diameter shafts used in medical applications. More precisely, the invention relates to a device for securely gripping a guide wire or hollow tube for a catheter.

In an angioplasty procedure, a guide wire is inserted into a patient's artery, and the guide wire is maneuvered to a stenosis or location of arterial blockage. Once the guide wire is in position across the blockage, a balloon catheter is advanced over the guide wire across the stenosis. The balloon catheter is then inflated to relieve the arterial constriction, deflated and then ultimately removed from the artery.

The maneuvering of a guide wire through the tortuous anatomy of the arterial system and across a lesion at the point of stenosis requires an operator to carefully "steer" the guide wire. This is accomplished by rotating the guide wire as it is advanced distally, so that a bent distal tip on the guide wire can be directed into the appropriate arterial branches. Because a typical guide wire is formed from a small diameter wire, it is difficult for the operator to grasp securely, and accordingly, it is difficult to control the degree of rotation thereof. Medical device manufacturers currently provide a variety of so called "guide wire gripping devices", or "torquers", or "handles" for use in gripping and manipulating the wires, but they all suffer from one or more deficiencies.

One example of such gripping devices is disclosed in Mar, U.S. Pat. No. 4,726,369, and is of a cylindrical body of resilient material with a slit in which the guide wire is received. An outer sleeve encircling the resilient body holds the slit closed over the wire. The major deficiency of this device is that it slips on the guide wire (both longitudinally and torsionally) and therefore prevents any direct correlation between rotation of the device and rotation of the guide wire.

Another example is shown in Auth, U.S. Pat. No. 4,829,999, which discloses a spring loaded gripping device to provide a more positive grip on the guide wire. The Auth patent device has a cylindrical body made of elastic material that has a longitudinal slot for receiving the guide wire. Handles are provided on either side of the slot for forcibly spreading the slot to receive the guide wire. The handles make the device awkward to manipulate, and the device also slips on the guide wire as torque is applied to the device.

SUMMARY OF THE INVENTION

The present invention is a device for gripping a proximal portion of an elongated medical shaft which is adapted to have a distal portion inserted into a patient's vascular system. The gripping device includes: a first generally planar shaft engagement surface which is aligned to extend longitudinally along the shaft, a second generally planar shaft engagement surface which is aligned parallel to and spaced from the first surface with the shaft aligned therebetween, and slide lock means for moving the second surface towards and longitudinally relative to the first surface to grip the shaft therebetween.

In one preferred embodiment of the gripping device, the first engagement surface is on a body member and a second engagement surface is on a sliding member. The slide lock means includes a first ramped surface on the body member and a second ramped surface on the sliding member which engages the first ramped surface, upon longitudinal movement of the sliding member relative to the body member, to move the first engagement surface towards the second engagement surface.

DETAILED DESCRIPTION OF THE PREFERRED EMBODIMENTS

Figure 1A:
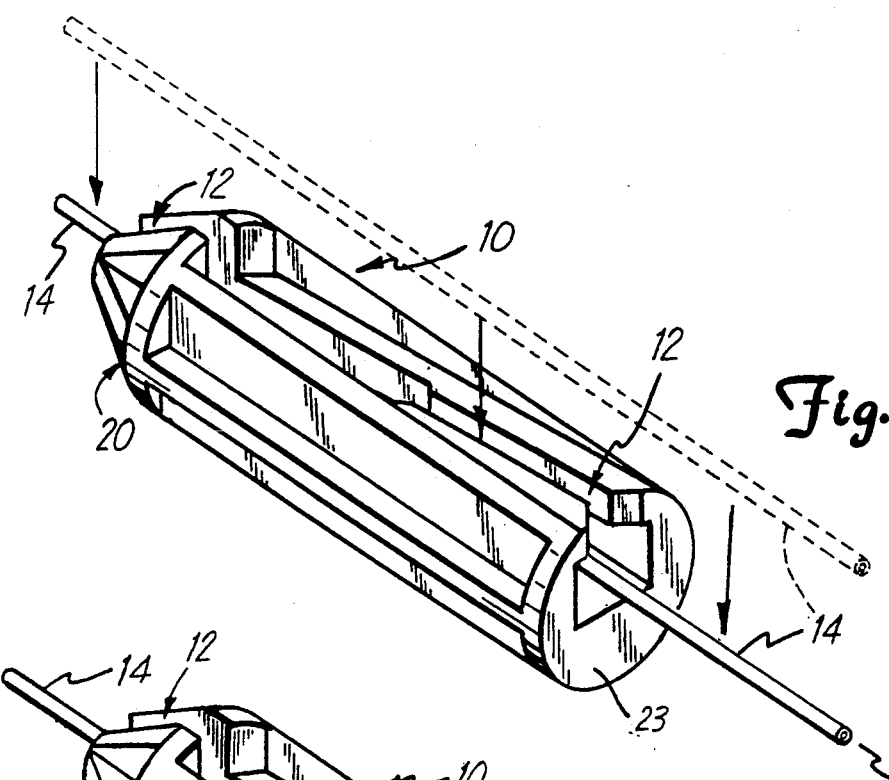
FIG. 1A shows the lateral installation of a medical shaft into a body member portion of a gripping device of the present invention.

As illustrated in FIG. IA, IB and IC, a gripping device 8 of the present invention has a generally cylindrical body member 10 with a longitudinal slot 12 for laterally receiving a medical shaft 14. A sliding member 16 is also received within slot 12 and is movable longitudinally relative to body member 10 to bring together a pair of opposed surfaces on body member 10 and sliding member 16 to hold medical shaft 14 tightly therebetween.

More specifically, in an angioplasty procedure a distal portion of medical shaft 14 (a guide wire or catheter tube) is inserted into a patient's vascular system, while the proximal portion of shaft 14 remains outside the patient's body. This proximal portion of shaft 14 is placed in slot 12 of body member 10 (FIG. 1A). Sliding member 16 is then inserted into body member 10 (FIG. IB) and is urged distally to engage shaft 14 between the opposed surfaces of body member 10 and sliding member 16 (FIG. IC). Once shaft 14 is so engaged, rotation of gripping device 8 rotates shaft 14 in a 1:1 relationship, which is important when steering shaft 14 through the patient's vascular system by twisting the proximal portion thereof to direct the advance of the distal portion of shaft 14.

Figure 1B:
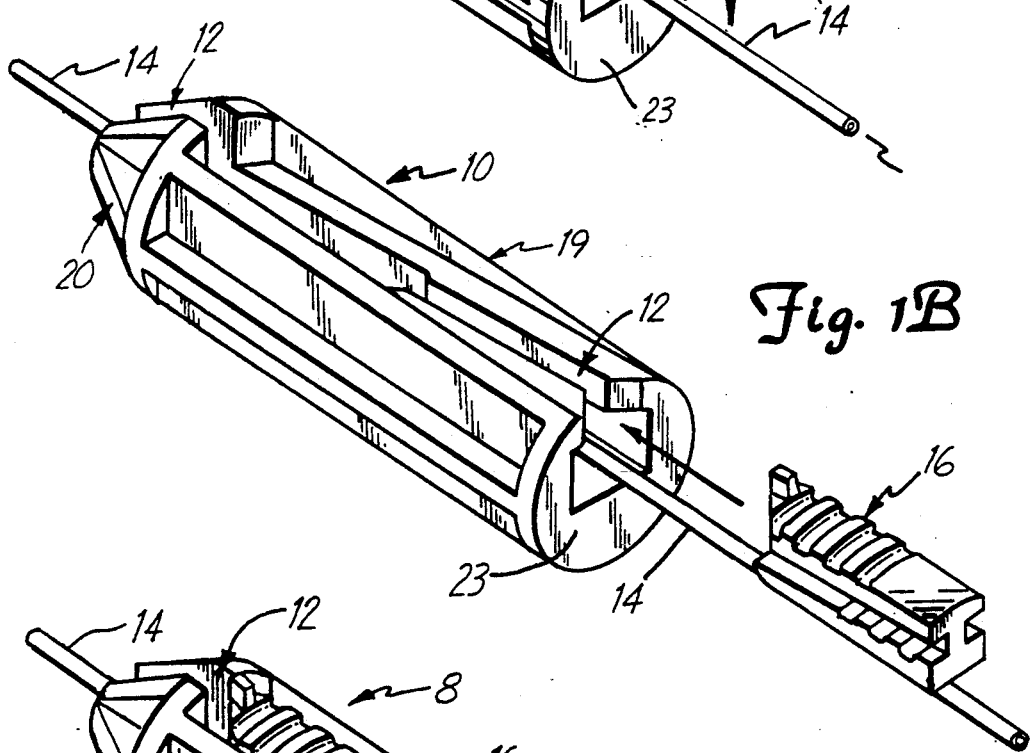
FIG. 1B shows the longitudinal insertion of a sliding member into the body member.
Figure 1C:
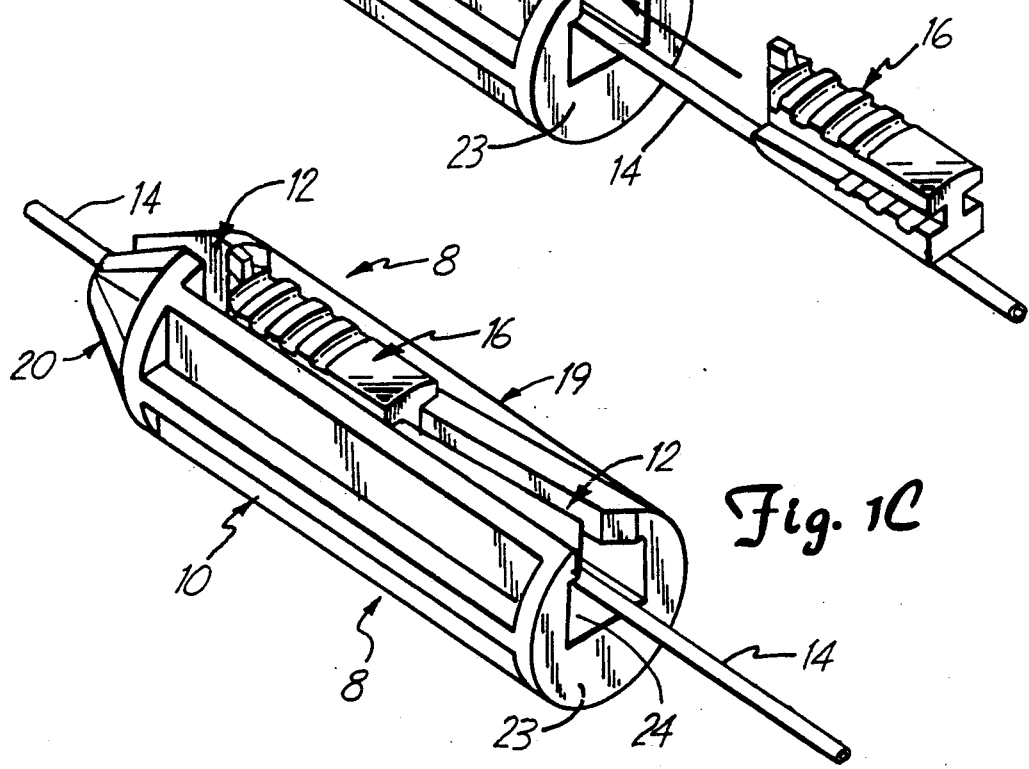
FIG. 1C shows the sliding member positioned relative to the body member so as to affirmatively grip the medical shaft.
Figure 2A:
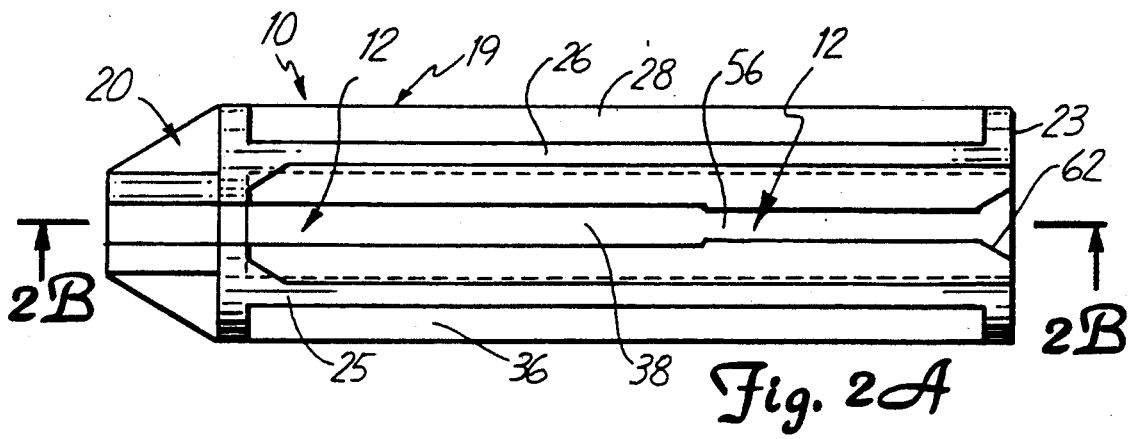
FIG. 2A shows a top plan view of the body member.
Figure 2B:
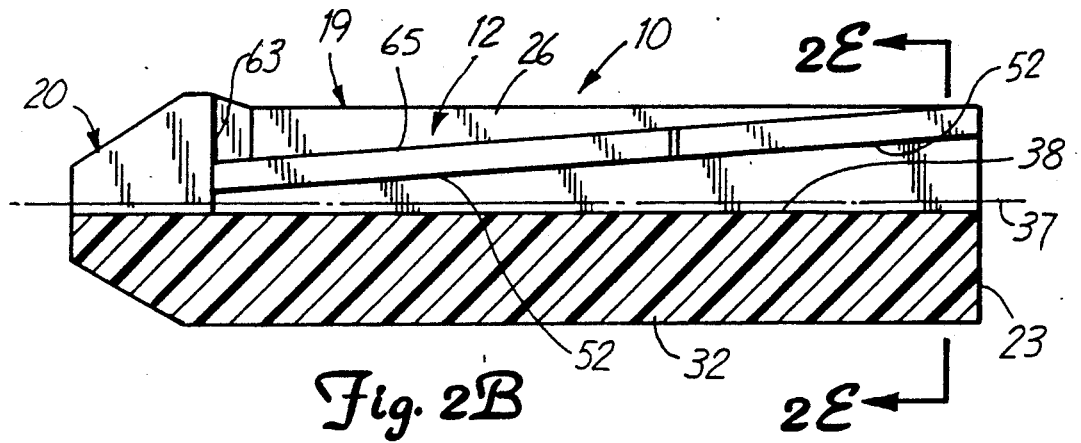
FIG. 2B shows a sectional view as taken along line 2B—2B in FIG. 2A.
Figures 2C, 2D, 2E:
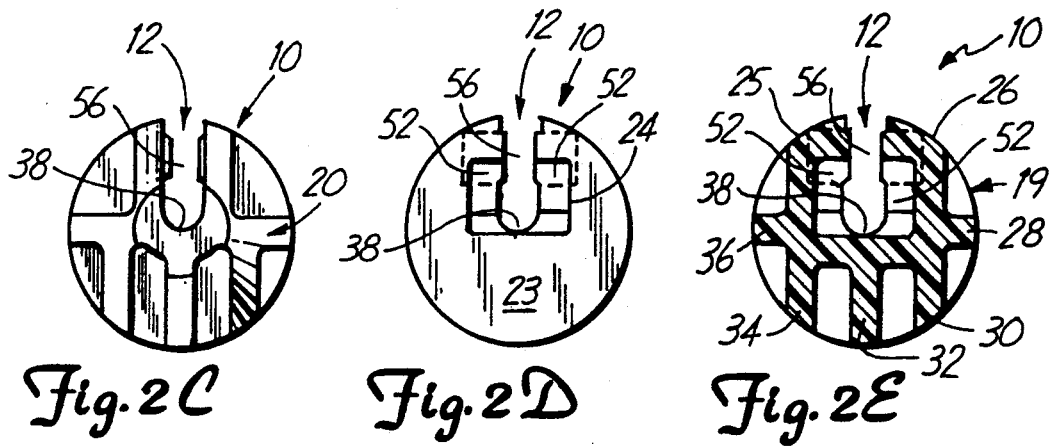
FIG. 2C shows a distal end view of the body member of FIG. 2A.
FIG. 2D shows a proximal end view of the body member of FIG. 2A.
FIG. 2E is a sectional view as taken along line 2E—2E in FIG. 2B.
Figure 3A:
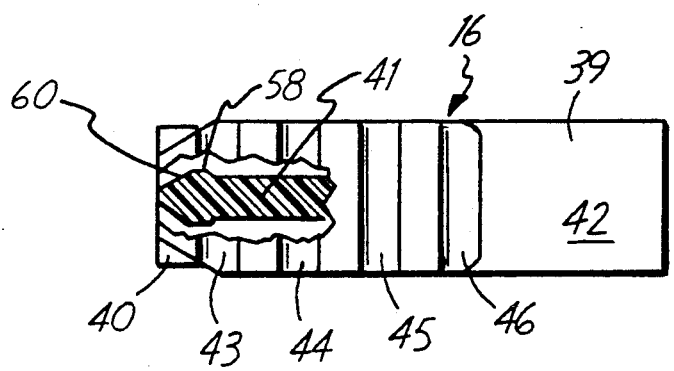
FIG. 3A shows a top plan view of the sliding member, with a portion of its distal end broken away and shown in section.
Figure 3B:
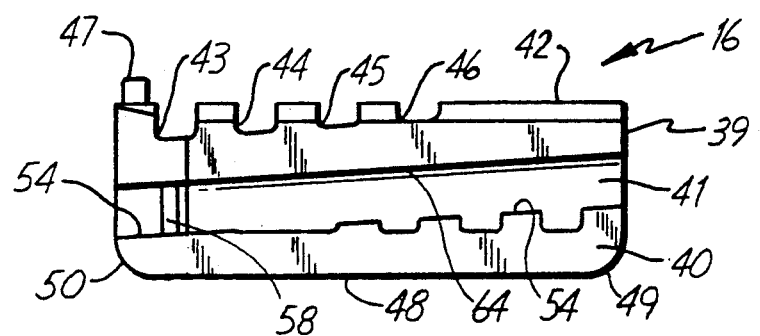
FIG. 3B shows a side view of the sliding member of FIG. 3A.
Figure 3C:
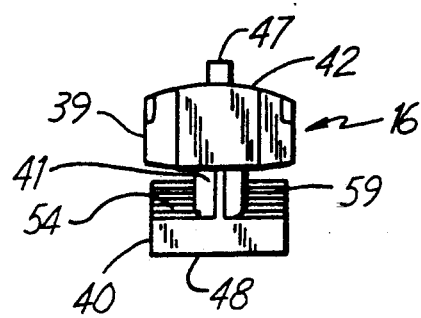
FIG. 3C shows a distal end view of the sliding member of 3A.

As noted above, body member 10 and sliding member 16 are the two components which comprise gripping device 8. Body member 10 is illustrated in FIGS. 2A-2E, while sliding member 16 is illustrated in FIGS. 3A-3C. Body member 10 has a generally cylindrical main portion 19 with a frusto-conical portion 20 at its distal end. At its proximal end, body member 10 has a laterally flat end wall 23 with an opening 24 therethrough and into slot 12 (see FIG. IC and FIG. 2D) for longitudinally receiving sliding member 16. The outer surface of cylindrical main portion 19 of body member 10 is defined by a plurality of longitudinal ribs 25, 26, 28, 30, 32, 34, and 36, as shown in FIGS. 1A, 1B, 1C, 2A, 2B, 2C and 2E. These longitudinal ribs facilitate manipulation of gripping device 8 and providing tactile feedback to the operator for determining the degree of rotation. As seen in FIG. 2A, 2B and 2C, distal portion 20 of body member 10 is also defined by a ribbed structure. The lack of material between all of these ribs lightens body member 10 and reduces its material requirements.

As best shown in FIGS. 2A and 2B, slot 12 extends longitudinally from proximal end wall 23 to distal portion 20, entirely through body member 10. Slot 12 extends laterally from the outer surface of body member 10, (between ribs 25 and 26) into body member 10 and slightly across a central longitudinal axis 37 thereof, as seen in FIG. 2B. A bottom surface 38 of slot 12 is flat (longitudinally), so that when medical shaft 14 is aligned within body member 10 (as seen in FIGS. 1A, 1B and 1C), it is engaged and supported by bottom surface 38 along the entire length of slot 12 without bending of shaft 14.

Sliding member 16, the other component of the gripping device 8, has an overall shape similar to an I-beam (see FIG. 3C), with an upper cross member 39, lower cross member 40 and central upright longitudinal beam 41. An upper, laterally arcuate surface 42 of upper member 39 has a series of lateral grooves 43, 44, 45 and 46 thereon, which provide an enhanced grip for the thumb or finger of an operator on sliding member 16. In addition, knob 47 on upper surface 42 (see FIG. 3B) provides a tactile feel indicator on sliding member 16, to permit an operator to determine the orientation of gripping device 8, or to count the number of rotations thereof in use. A bottom surface 48 of lower member 40 is centrally flat, with rounded proximal and distal end corners 49, 50.

The operative, opposed surfaces of gripping device 8 include bottom surface 38 of slot 12 on body member 10 (as shown in FIG. 2B) and bottom surface 48 on sliding member 16 (as shown in FIG. 3B). When gripping device 8 is assembled for use, these two opposed engagement surfaces are urged together to "trap" medical shaft 14 therebetween, thereby securing gripping device 8 to shaft 14.

Engagement surfaces 38 and 48 are brought together about medical shaft 14 by a slide lock arrangement comprised of ramped surface 52 on body member 10 (see FIG. 2B) and ramped surface 54 on lower cross member 40 of sliding member 16 (via opening 23) (see FIG. 3B). Ramped surface 52 has portions on each side of slot 12 (see FIGS. 2D and 2E) and ramped surface 54 has portion on each side of center beam 41 (see FIG. 3C). Longitudinal insertion of sliding member 16 into slot 12 of body member 10 causes ramped surface 54 on sliding member 16 to engage ramped surface 52 on body member 10, and as sliding member 16 is continually urged toward the distal end of body member 10, these two ramped surfaces 52 and 54 continue to engage. As a result, sliding member 16 is urged laterally "downwardly" into slot 12 as sliding member 16 moves toward the distal end of body member 10. Consequently, engagement surfaces 38 and 48 are urged together. In a preferred embodiment each ramped surface is offset by approximately four degrees from its respective engagement surface (34, 48).

Upon assembly of body member 10 and sliding member 16, the opposed ramped surfaces 52 and 54 are generally in engagement. Opposed engagement surfaces 38 and 48 do not, in operation, engage one another and are at all times generally parallel and spaced apart. As sliding member 16 is moved distally in slot 12, its bottom surface 48 moves laterally toward bottom surface 38 of slot 12 (until both surfaces affirmatively engage medical shaft 14 which is disposed within slot 12). At the same time, bottom surface 48 moves longitudinally relative to bottom surface 38, although throughout such movement, these opposed surfaces 38 and 48 remain generally parallel. There is thus no one point of extreme gripping pressure exerted on medical shaft 14, but rather gripping pressure applied along the entire length of bottom surface 48 of sliding member 16.

To prevent sliding member 16 from inadvertently separating from body member 10, a narrowing or constriction 56 of slot 12 at the proximal end of body member 10 (see FIG. 2A) is provided, along with an enlarged flange 58 on a tapered distal portion 60 of central beam 41 of sliding member 16 (see FIG. 3A). As shown in FIG. 2A, an outwardly flared portion 62 of slot 12 at its proximal end facilitates reception of tapered distal portion 60 of central beam 41 of sliding member 16. Additional force is required to move sliding member 16 through the constricted portion 56 of slot 12 on body member 10 because it is narrower than the width of flange 58. To accommodate this, body 10 spreads slightly apart at constricted portion 56 of slot 12 when sliding member 16 is passed through constricted portion 56. Once enlarged flange 58 is distally past slot constriction 56, however, flange 58 acts as a stop (engaged by constriction 56) to prevent sliding member 16 from being inadvertently moved out of slot 12 in a proximal direction.

In a preferred embodiment, body member 10 of gripping device 8 is formed from molded polycarbonate, and sliding member 16 is formed from molded polyvinylchloride (PVC). The PVC sliding member 16 is thus softer than the polycarbonate body member 10, and upon being urged into engagement with shaft 14, lower cross member 41 of sliding member 16 will deform slightly about shaft 14 and between surfaces 52 and 38 of body member 10. This deformation aids the gripping device 8 in making an affirmative no-slip grip on shaft 14. Of course, in another embodiment, body member 10 can be formed from a softer material than sliding member 16 and the gripping effect on shaft 14 will be essentially the same. It is preferred (although not necessarily essential) that one of the opposed components be capable of some deformation upon moving sliding member 16 into engagement with shaft 14 in order to achieve the desired "lock-down" effect of gripping device 8 on shaft 14.

The polycarbonate material used to form body member 10 is opaque, but can be made transparent to allow an operator to verify the position and engagement of medical shaft 14 in gripping device 8. In addition, gripping device 8 is useable on a solid medical shaft (such as a guide wire) or a high-strength hollow tube shaft (such as a stainless steel hypotube).

In operation, sliding member 16 is removed from body member 10, and medical shaft 14 is inserted laterally into the longitudinal slot 12 of body member 10 (preferably with body member 10 orientated such that its distal end extends distally along medical shaft 14), as illustrated in FIG. 1A. Sliding member 16 is inserted longitudinally into opening 23 and slot 12 at the proximal end of body member 10, as illustrated in FIG. 1B, and such as, sliding member 16 is aligned over shaft 14 in slot 12. Sliding member 16 is then urged distally along body member 10 which causes ramped surfaces 52 and 54 to engage, thereby urging opposed engagement surfaces 38 and 48 toward one another. Eventually, opposed surfaces 38 and 48 are urged so close together that shaft 14 therebetween is effectively trapped and engaged, along the entire length of bottom surface 48 on sliding member 16. Sliding member 16 is retained in this position relative to body member 10 by the friction forces acting on their respective opposed ramped surfaces 54 and 52, and the friction forces acting between shaft 14 and opposed engagement surfaces 48 and 38.

Once gripping device 8 has engaged medical shaft 14 (as shown in FIG. 1C), body member 10 can be manipulated by the doctor and rotated to turn and steer medical shaft 14 as it is inserted into a patient's vascular system. During the insertion process, gripping device 8 can easily be removed and/or repositioned on shaft 14 as desired. The gripping device 8 is repositioned by moving the sliding member 16 toward the proximal end of body member 10 but not out of slot 12, which separates opposed surfaces 38 and 48. In this contra engagement movement, an upper set of opposed ramped surfaces 64 and 65 on sliding member 16 and body member 10, respectively, engage to urge opposed engagement surfaces 38 and 48 apart as sliding member 16 moves proximally relative to body member 10. This separation, which places the slide lock in an "open" position, allows gripping device 8 to be slid freely along medical shaft 14 to another desired position. Once repositioned, sliding member 16 is moved distally on body member 10 to once again firmly grip medical shaft 14, thereby placing the slide lock in a "closed" position.

Gripping device 8 is removed from shaft 14 simply by first urging sliding member 16 toward and past the proximal end of body member 10, thereby separating sliding member 16 from body member 10 and opening up slot 12. Medical shaft 14 is then simply "lifted" out of longitudinal slot 12 on body member 10.

A second preferred embodiment 108 of the gripping device of the present invention is illustrated in FIGS. 4A–4E. Unless otherwise mentioned, this second embodiment has the same construction and features as the embodiment discussed above, and for those unchanged features, the same reference numerals are used herein. In this second embodiment, the sliding member is preferably unchanged, but the body member has a different longitudinal slot configuration. An offset, longitudinally extending slot 105 is added to slot 12 of a body member 110 for lateral reception of medical shaft 14. By providing a separate slot 105, this embodiment does not require the removal of sliding member 16 for loading and unloading gripping device 108 onto medical shaft 14.

Figure 4A:
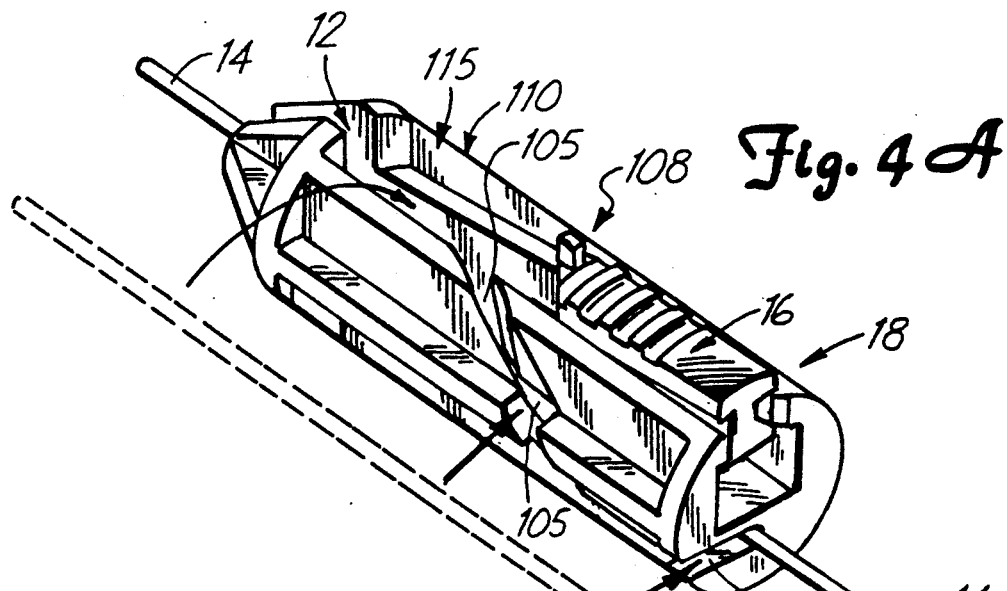
FIG. 4A shows, in perspective, the lateral installation of a medical shaft into a body member of another preferred embodiment of the gripping device of the present invention.
Figure 4B:
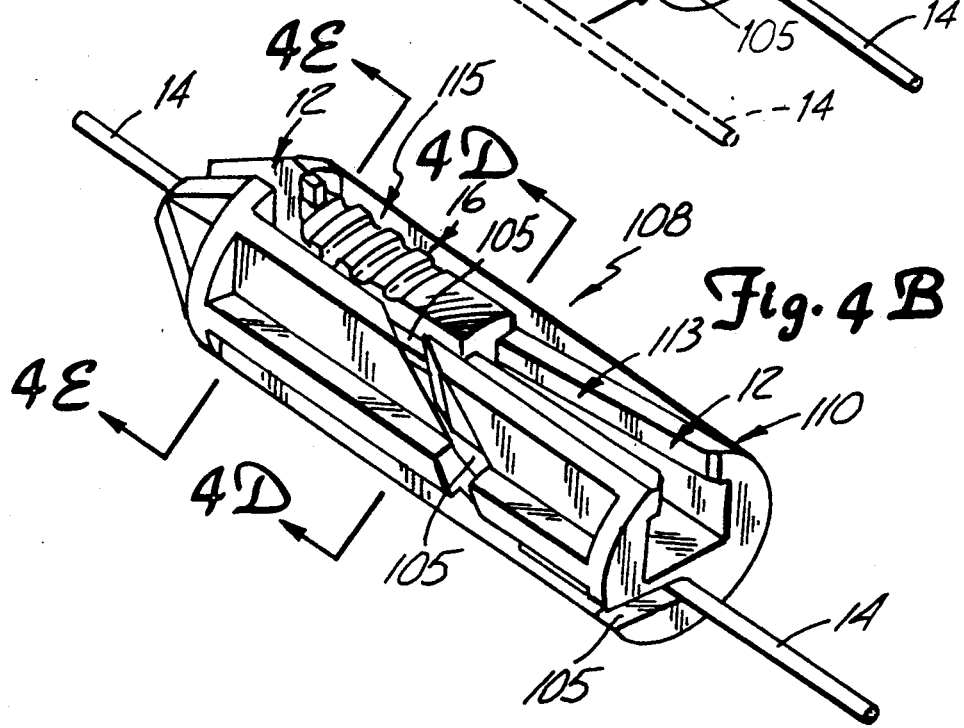
FIG. 4B shows the sliding member positioned relative to the body member of FIG. 4A so as to affirmatively grip the medical shaft.
Figures 4C, 4D, 4E:
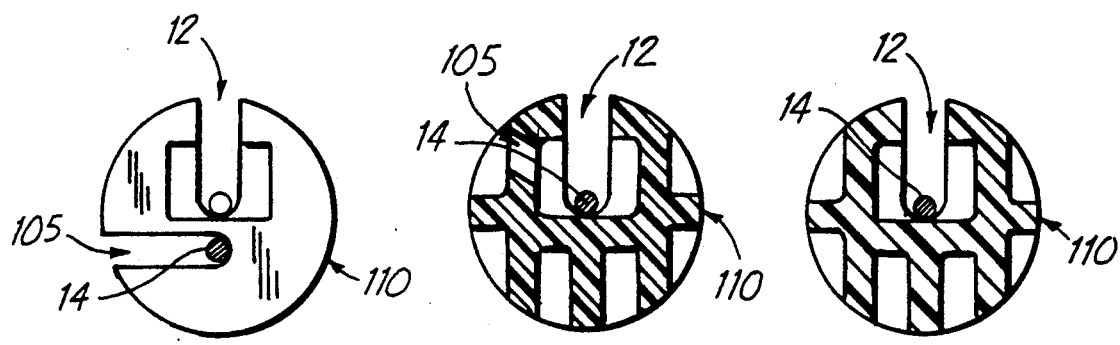
FIG. 4C shows a proximal end view of the body member of FIG. 4A.
FIG. 4D is a sectional view of the body member as taken along lines 4D—4D in FIG. 4B.
FIG. 4E is a sectional view of the body member as taken along line 4E—4E in FIG. 4B.

As illustrated in FIGS. 4A, 4B and 4C, offset slot 105 is aligned "below" slot 12 in body member 110 at the proximal end of body member 110, and accordingly, body member 110 has more structure for supporting slot 105 and slot 12 than body member 10 of the first embodiment compare FIGS. 4D and 2E). As offset slot 105 passes distally through body member 110, it spirals "upwardly" (compare FIGS. 4B and 4D) until it is in alignment with and becomes slot 12 (see FIG. 4E), at approximately the longitudinal midpoint of body member 110.

Thus, sliding member 16 can be retained within slot 12, in a proximal section 113 thereof (see FIGS. 4A and 4B), while slot 105 and a distal section 115 of slot 12 are open for lateral reception of medical shaft 14. In this position, the slide lock is in its "opened" position. This embodiment thus allows loading and unloading of medical shaft 14 on body member 110 without the proximal disengagement of sliding member 16 from body member 110.

Operation and use of this second embodiment 108 of gripping device is as follows. Sliding member 16 must first be moved to the proximal section 113 of slot 12 on body member 110, thereby allowing medical shaft 14 to be inserted laterally into offset slot 105 and distal section 115 of slot 12, as shown in FIG. 4A. Medical shaft 14 experiences a slight bend as it traverses slot 105 and distal section 115 of slot 12, but the bend is very gentle and not abrupt enough to kink or damage medical shaft 14. The slide lock arrangement operates in the same manner as discussed above, with counteracting ramped surfaces on the sliding member 16 and body member 110 to urge opposed generally parallel engagement surfaces laterally toward one another as sliding member 16 is moved longitudinally along body member 110 in a distal direction. Medical shaft 14 is thus firmly gripped between the opposed engagement surfaces simply by moving sliding member 16 toward the distal end of body member 110, as illustrated in FIG. 4B. In this position, the slide lock is in its "closed" position.

Once the gripping device 108 of this second embodiment has been attached to medical shaft 14, body member 110 can be gripped by the doctor and rotated to turn and steer medical shaft 14 as it is inserted into a patient's vascular system. During the insertion process, gripping device 108 can be removed and repositioned on shaft 14 as desired, simply by moving sliding member 16 toward the proximal end of body member 110 to place the slide lock in its "open" position. Gripping device 108 is then free to be repositioned along medical shaft 14, or it can be removed therefrom simply by lifting the shaft 14 from offset slot 105 and distal section 115 of slot 12.

The gripping device of the present invention has a number of important features and advantages. It can be attached to a medical shaft laterally at any point along the medical shaft. It is easy to install and remove, it gives the doctor good control over the rotational position of the shaft and it provides a positive and dependable grip on the shaft. The gripping device of the present invention is lightweight, conforms to the hand, and provides tactile feedback to the doctor for determining orientation of the gripping device. In addition, once installed, the gripping device is repositionable on the shaft with one hand.

Although the present invention has been described with reference to preferred embodiments, workers skilled in the art will recognize that changes may be made in form and detail without departing from the spirit and scope of the invention. For example, although a sliding surface arrangement is shown as the preferred means for moving the engagement surfaces together in a parallel manner, other mechanisms for achieving this end (e.g., a cam-driven structure) would work as well.

What is claimed is:

1. A device for gripping a proximal portion of an elongated medical shaft which is adapted to have a distal portion thereof inserted into a patient's vascular system, the device comprising:
   a first generally planar shaft engagement surface for extending longitudinally along a shaft, the first shaft engagement surface forming a single continuous plane extending longitudinally from a proximal end to a distal end of the device;
   a second generally planar shaft engagement surface which is parallel to and spaced from the first surface for aligning a the shaft therebetween; and
   a slide arrangement for moving the second surface toward and longitudinally relative to the first surface to grip a shaft therebetween, wherein the first and second surfaces remain substantially parallel to each other during sliding movement to prevent the shaft from being kinked between the first and second surfaces during gripping of the shaft.

2. The device of claim 1, and further comprising:
   a body member having the first engagement surface thereon;
   a sliding member having the second engagement surface thereon; and
   wherein the slide arrangement includes a first ramped surface on the body member, and a second opposed ramped surface on the sliding member which engages the first ramped surface, upon longitudinal movement of the sliding member relative to the body member, to move the first engagement surface toward the second engagement surface.

3. The device of claim 2 Wherein the member is disengagable from the body member, from a proximal end of the body member.

4. The device of claim 2 wherein the body member has a substantially cylindrical outer surface.

5. The device of claim 2 wherein the body member has a generally cylindrical shape with a generally longitudinal slot along one side thereof, and further comprising:
   means for removably retaining the sliding member within that slot for longitudinal movement relative to the body member.

6. The device of claim 5 wherein the longitudinal slot in the body member defines means for laterally inserting the body member onto a shaft when the sliding member has been removed from the body member.

7. The device of claim 5 wherein the longitudinal slot is a first slot and wherein the body member has a second generally longitudinal slot which is open adjacent its distal end to the first slot.

8. The device of claim 7 wherein the second slot and a distal portion of the first slot define means for laterally inserting the body member onto a shaft when the sliding member is within a proximal portion of the first slot.

9. The device of claim 2 wherein an outer surface of the body member has at least one longitudinal rib thereon to facilitate grasping and manipulation of the body member.

10. The device of claim 2, wherein the body member has a generally longitudinally extending slot for receiving a shaft.

11. The device of claim 2 wherein the sliding member has a plurality of lateral grooves thereon to facilitate movement of the sliding member relative to the body member.

12. The device of claim 1 wherein the device has a raised knob on an outer surface thereof to facilitate manipulation of the slide arrangement.

13. The device of claim 2 wherein the body member is made of polycarbonate and the sliding member is made of polyvinylchloride.

14. In a combination of a device and an elongated medical shaft, the device having a first surface and an opposed second surface for gripping a proximal portion of an elongated medical shaft which is adapted to have a distal portion thereof inserted into a patient's vascular system, the improvement which comprises:
   a surface movement and lock mechanism for moving the first surface toward and longitudinally relative to the second surface to grip the shaft therebetween, the first shaft engagement surface forming a single continuous plane extending longitudinally from a proximal end to a distal end of the device, wherein the first and second shaft engagement surfaces which grip the shaft are broader than a diameter of the shaft.

15. The device of claim 14 wherein the slide arrangement has a first open position wherein the first and second engagement surfaces are spaced apart sufficient to permit free movement of the shaft therebetween, and a second closed position wherein the first and second engagement surfaces are moved together to grip the shaft with a clamping force sufficient such that rotating the device about an axis defined by the shaft imparts the same amount of axial rotation to the shaft itself.

16. The device of claim 14 wherein the shaft is a guide wire.

17. The device of claim 14 wherein the shaft is a tube.

18. The device of claim 17 wherein the tube is stainless steel.

19. A device for gripping a proximal portion of an elongated medical shaft which is adapted to have a distal portion thereof inserted into a patient's vascular system, the device comprising:
   a body member having a first generally planar shaft engagement surface for extending longitudinally along a shaft, the first shaft engagement surface forming a single continuous plane extending longitudinally from a proximal end to a distal end of the device;
   a sliding member having a second generally planar shaft engagement surface parallel to and spaced from the first surface for aligning a shaft therebetween; and
   a slide arrangement for moving the second surface toward and longitudinally relative to the first surface to grip a shaft therebetween, the slide arrangement including a first ramped surface on the body member and a second opposed ramp surface on the sliding member which engages the first ramped surface upon longitudinal movement of the sliding member relative to the body member to move the first engagement surface toward the second engagement surface, and the two opposed ramped surfaces being disposed at an angle relative to the first and second engagement surfaces of approximately four degrees.

20. A method for attaching a gripping device onto a proximal portion of an elongated medical shaft having a distal portion adapted to be inserted into a patient's vascular system which comprises the steps of:

(a) aligning a first member so that a first generally planar surface thereof lies longitudinally along the shaft and forms a single continuous plane that extends longitudinally from a proximal end to a distal end of the gripping device;

(b) aligning a second member so that a second generally planar surface thereof is generally parallel to and spaced from the first surface of the first member, with the shaft extending therebetween; and (c) moving the second surface toward and longitudinally relative to the first surface to secure the shaft therebetween and secure the first member with respect to the second member, wherein the first and second surfaces which grip the shaft are broader than a diameter of the shaft.

21. The method of claim 20 wherein the first member has a generally longitudinally extending slot therein for reception of the shaft, and wherein step (a) includes placing the shaft laterally into the slot on the first member.

22. A method for attaching a gripping device on a proximal portion of an elongated medical shaft having a distal portion adapted to be inserted into a patient's vascular system which comprises the steps of:

(a) providing a first member having a first generally longitudinal slot and a second generally longitudinal slot which is open adjacent its distal end to the first slot and is offset from the first slot;

(b) providing a second member slidably moveable within and longitudinally relative to the first slot, the second member being retained within the first slot;

(c) sliding the second member to a proximal end of the first member;

(d) inserting the shaft laterally into the first and second slots along the entire length of the first member; and (e) sliding the second member toward a distal end of the first member to secure the shaft between the first and second members.

23. The device of claim 2 and further comprising: means for selectively constraining longitudinal movement of the sliding member relative to the body member.

24. A device for gripping a proximal portion of an elongated medical shaft which is adapted to have a distal portion thereof inserted into a patient's vascular system, the device comprising:

a body member having a first generally planar shaft engagement surface for extending longitudinally along a shaft and having a generally cylindrical shape with a generally longitudinal slot along one side thereof;

a sliding member disposed within the slot for longitudinal movement relative to the body member, the sliding member having a second generally planar shaft engagement surface parallel to and spaced from the first surface for aligning a shaft therebetween;

a slide arrangement for moving the second surface toward and longitudinally relative to the first surface to grip a shaft therebetween, the slide arrangement including a first ramped surface on the body member and a second opposed ramp surface on the sliding member which engages the first ramped surface upon longitudinal movement of the sliding member relative to the body member to move the first engagement surface toward the second engagement surface; and a flange formed on the sliding member and a constriction formed in the slot of the body member, the flange frictionally engaging the constriction such that the sliding member snaps through the constriction to be retained within the slot distally of the constriction.

25. A device for gripping a proximal portion of an elongated medical shaft which is adapted to have a distal portion thereof inserted into a patient's vascular system, the device comprising:

a body member having a first generally planar shaft engagement surface for extending longitudinally along a shaft and having a generally cylindrical shape with a longitudinal slot along one side thereof;

a sliding member disposed within the slot for movement relative to the body member, the sliding member having a generally planar shaft engagement surface parallel to and spaced from the first surface for aligning a shaft therebetween, and the sliding member being moveable within and relative to the body member between a shaft gripping position and a shaft loading position;

a slide arrangement for moving the second surface toward and longitudinally relative to the first surface to grip a shaft therebetween;

wherein the shaft is insertable laterally into the slot of the body member only when the sliding member is moved to its shaft loading position.

* * * * *